(12) United States Patent
Ostojic

(10) Patent No.: US 8,221,436 B2
(45) Date of Patent: Jul. 17, 2012

(54) APPARATUS AND METHOD FOR POSITIONING AND ORIENTATION OF MEDICAL INSTRUMENTS

(75) Inventor: Mile Ostojic, London (CA)

(73) Assignee: National Research Council of Canada, Ottawa ON ( * ) Notice: Subject to any disclaimer, the term of this patent is extended or adjusted under 35 U.S.C. 154(b) by 1073 days.

(21) Appl. No.: 11/583,697

(22) Filed: Oct. 20, 2006

(65) Prior Publication Data

US 2008/0097413 A1 Apr. 24, 2008

(51) Int. Cl.
*A61B 19/00* (2006.01)
*A61M 36/00* (2006.01)

(52) U.S. Cl. .......................... 606/130; 600/7

(58) Field of Classification Search ............ 606/129, 606/130, 1; 600/7, 8; 602/32; 128/98.1, 128/103.1, 845; 604/116; 74/479.01, 479.03, 74/490.01, 490.03, 490.05; 901/14–16
See application file for complete search history.

(56) References Cited

U.S. PATENT DOCUMENTS

| | | | | |
|---|---|---|---|---|
| 4,535,763 A | * | 8/1985 | Jaquet | 606/56 |
| 5,871,448 A | * | 2/1999 | Ellard | 600/459 |
| 6,047,610 A | * | 4/2000 | Stocco et al. | 74/479.01 |
| 6,398,711 B1 | | 6/2002 | Green et al. | |
| 6,540,656 B2 | | 4/2003 | Fontayne et al. | |
| 6,702,761 B1 | | 3/2004 | Damadian et al. | |
| 6,712,782 B2 | | 3/2004 | Ford | |
| 6,723,106 B1 | * | 4/2004 | Charles et al. | 606/130 |
| 6,752,753 B1 | | 6/2004 | Hoskins et al. | |
| 6,846,282 B1 | | 1/2005 | Ford | |
| 6,869,390 B2 | | 3/2005 | Elliott et al. | |
| 7,604,645 B2 | * | 10/2009 | Barzell et al. | 606/130 |
| 2002/0007103 A1 | * | 1/2002 | Fontayne et al. | 600/7 |

FOREIGN PATENT DOCUMENTS

WO  WO 98/56295  12/1998

OTHER PUBLICATIONS

Stocco, et al., IEEE/ASME Transactions on Mechatronics, vol. 6, No. 3, Sep. 2001, pp. 210-220.

* cited by examiner

*Primary Examiner* — Tuan Nguyen
*Assistant Examiner* — Thomas McEvoy
(74) *Attorney, Agent, or Firm* — Jason E. J. Davis

(57) ABSTRACT

This invention relates to a method and an apparatus for positioning, orientation and insertion of a medical device. The apparatus comprising a first pentagonal mechanism which offers two degrees of freedom, and a second pentagonal mechanism which offers three degrees of freedom of motion. The two are aligned along a first axis so as to permit them to hold an instrument driving means. The instrument driving means is adapted to hold a medical instrument and adapted to permit said instrument to move along and rotate on its own axis. The instrument driving means offers another two degrees of freedom of motion. The apparatus provides a total of six degrees of freedom.

15 Claims, 2 Drawing Sheets

Schematic of the proposed apparatus

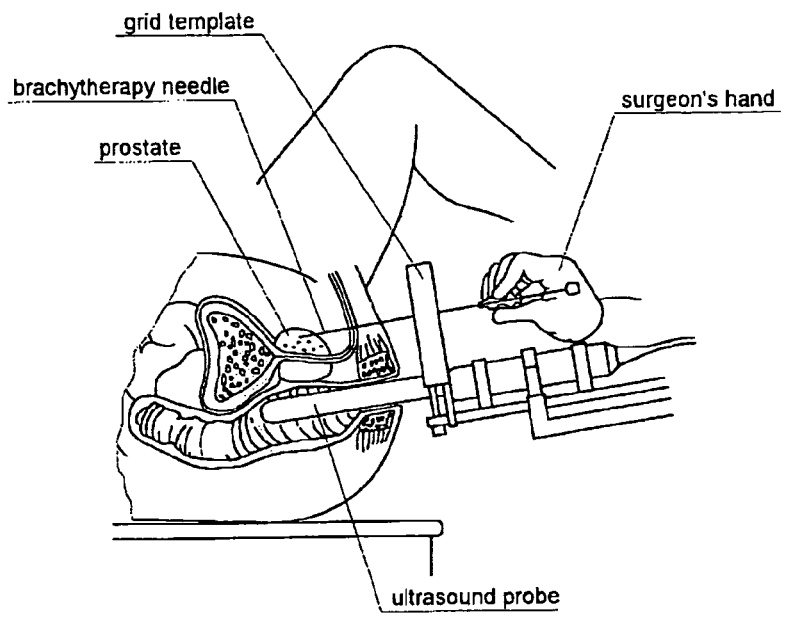
Figure 1 (PRIOR ART). Conventional brachytherapy
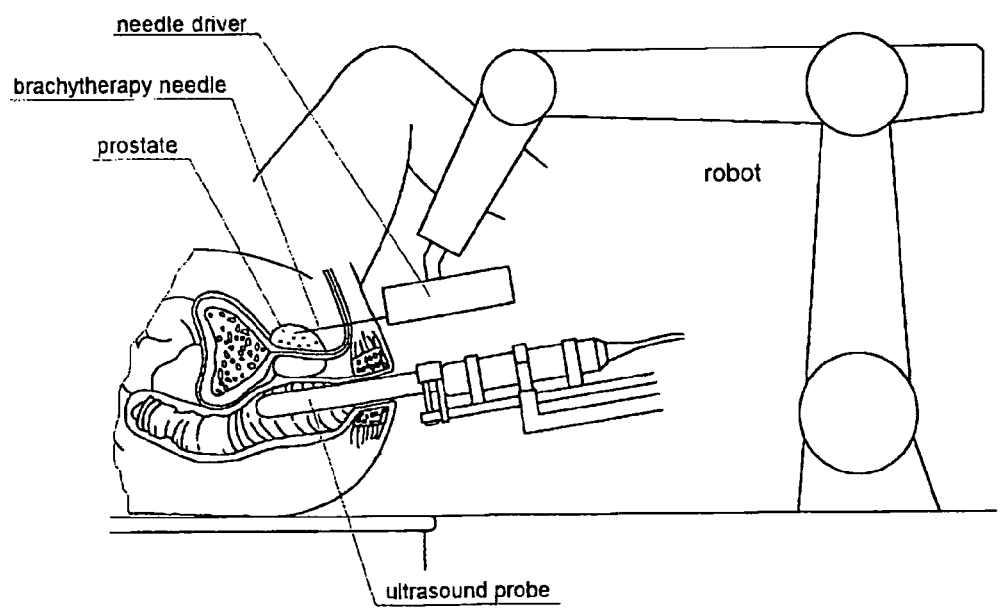
Figure 2 (PRIOR ART). Robot-assisted brachytherapy

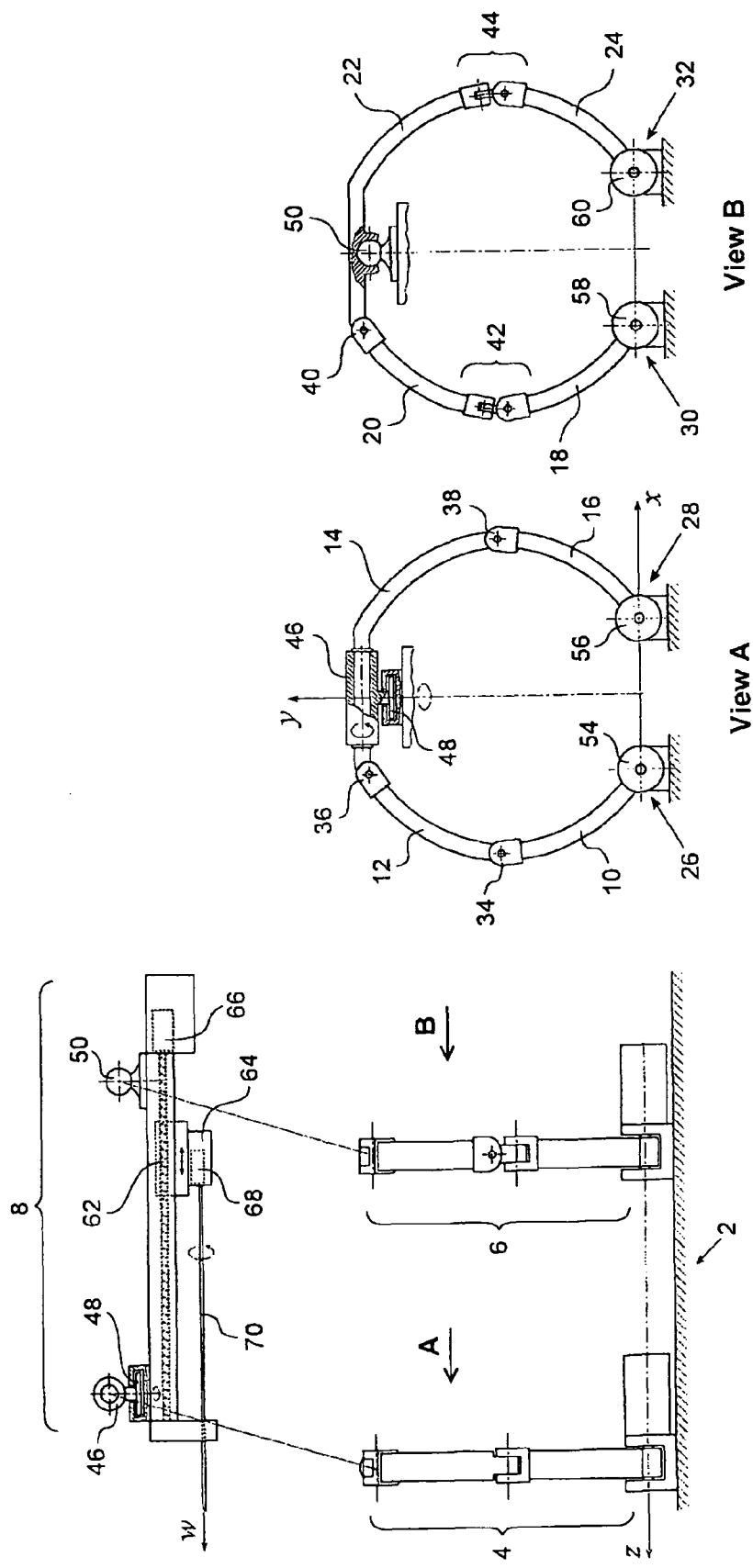
Figure 3. Schematic of the proposed apparatus

APPARATUS AND METHOD FOR POSITIONING AND ORIENTATION OF MEDICAL INSTRUMENTS

FIELD OF THE INVENTION

This invention relates to an apparatus and method for positioning, orientation and insertion of a medical instrument. More specifically this application relates to an apparatus that enables positioning, orientation and insertion of medical instruments such as needles or laser sources.

BACKGROUND

On average 2,944 Canadians will be diagnosed with cancer every week, of that an average of 1,354 Canadians will die of it every week. Based on the current incidence rates, 38% of Canadian women will develop cancer during their lifetimes, and a staggering 44% of men.

One method for treating certain cancers is to use internal or interstitial radiation therapy, or seed therapy, in which a radioactive implant is placed directly into a tumor. It involves surgical insertion of radiation source (radioactive seeds) into the treatment volume through tubular needles. Tubular needles loaded with radioactive seeds are inserted into the treatment volume, after which the radioactive seeds are left in the treatment volume, either permanently or for a specified amount of time. This method is called brachytherapy. Brachytherapy is used to treat various types of cancer throughout the human body, including the prostate, breast, cervix, and lungs.

Documented brachytherapy procedure is performed manually: the surgeon inserts brachytherapy needles into the cancerous tissue by hand, pushing them through holes in a specially prepared grid template (illustrated in FIG. 1).

U.S. Pat. No. 6,398,711 by Green et al., teaches the use of such a needle grid template.

U.S. Pat. No. 6,540,656 by Fontayne et al. discusses a targeting fixture again making use of a grid template. But this fixture can only provide 2-dimensional, translatory positioning of the instrument before insertion.

Another instrument making use of the grid template is illustrated in PCT application WO98/56295 by Fanucci.

The main drawback of the manual procedure is that it is slow and not very accurate. The distance between two adjacent holes in the grid template limits achievable accuracy of needle tip placement. Further, as the holes in the grid template are long (compared with their diameter) and all parallel to each other, oblique trajectories of needle insertion are not achievable. To compensate for this, the surgeon would typically press the needle by hand from a side and/or rotate it during insertion. The surgeon does this while monitoring the actual position of the needle in a real-time image (typically collected by transrectal ultrasound imaging system) so the overall procedure is involved, requires extensive training, and takes time.

An emerging modality is the use of a robotic manipulator and a special end-effector called "needle driver" to perform the procedure (FIG. 2). In robot-based systems, the robot is used to achieve quick and precise positioning and orientation of the needle driver (together with the brachytherapy needle that it holds). Once the specified position and orientation are achieved, the needle driver pushes the needle into the cancerous tissue. To increase the accuracy of the needle tip reaching the specified point inside the treatment volume, the needle may also be rotated along its axis during the insertion. Both the axial and rotary motion of the needle are driven by the needle driver.

Robot-based systems resolve some of the problems associated with manual brachytherapy such as the coarse spacing among the holes in a grid template and they allow for oblique insertion trajectories. However, they have some drawbacks of their own:

The robot takes a lot of space, it gets into surgeon's way, and its presence and motion can be intimidating to medical personnel involved in the procedure.
 Integrating the robot with the rest of the brachytherapy system (particularly the ultrasound imaging system) is difficult as the robot is physically detached from the rest of the system. The integration requires precise mounting of the robot as well as calibration of the complete system.
 The robot-based system is complex and the medical team needs extensive training to learn how to use it.
 Typically the robot has a large working area which can be hazardous (for example, it can hit the patient and/or surgeon if a large move is commanded by accident). Therefore the size of the robot's workspace has to be constrained by some safe means (typically by mechanical means).

The needs highlighted above are mostly for brachytherapy systems, but there are other medical instruments which require precise positioning and orientation. For example the proper positioning of a high-power laser source used for the treatment of enlarged prostate in a procedure termed benign prostate hyperplasia (BPH) is also needed.

SUMMARY OF THE INVENTION

It is an object of the invention to offer an apparatus that provides precise positioning and orientation of a medical instrument.

It is another object of the invention to achieve oblique trajectories for a medical instrument; making it possible to attain hard to reach places.

It is another object of the invention to offer a less obtrusive apparatus, leaving space for the surgeon and medical staff to access the operating site.

It is another object of the invention to offer an apparatus which can be integrated with existing medical systems.

These and other objects of the invention are accomplished by an apparatus for the positioning and orientating of a medical instrument, comprising a first pentagonal mechanism which offers two degrees of freedom, and a second pentagonal mechanism which offers three degrees of freedom of motion. The two are aligned along a first axis so as to permit them to hold an instrument driving means.

The instrument driving means is adapted to hold a medical instrument and adapted to permit said instrument to move along and rotate on its own axis. The instrument driving means offers another two degrees of freedom of motion. The apparatus is thus provided with a total of six degrees of freedom.

SHORT DESCRIPTION OF THE FIGURES

FIG. 1 (prior art) illustrates an embodiment of a brachytherapy method using a manual procedure FIG. 2 (prior art) illustrates an embodiment of brachytherapy method using a robot FIG. 3 illustrates an embodiment of the apparatus for positioning and orienting a medical device

DETAILED DESCRIPTION OF THE INVENTION

This invention proposes the replacement of the serial-linkage robot with a specially designed parallel-kinematics mechanism. The parallel-kinematics mechanism is designed as a compact device that is easy to integrate with the rest of the medical systems (for example, it can be permanently integrated with the brachystepper mechanism used for support and positioning of the ultrasound imaging probe). Furthermore, the size of its workspace is easily kept within desired limits by the design of its linkages, which significantly reduces hazards associated with the use of actuated devices in brachytherapy procedures.

An embodiment of this invention is illustrated in FIG. 3. It illustrates an apparatus for positioning and orientating a medical instrument. The apparatus offers a total of six degrees of freedom which allow for the maneuverability and precision sought after in medical interventions.

Illustrated is a first and a second pentagonal mechanism (4 and 6 respectively) fixed to a base (2). The first pentagonal mechanism offers two degrees of freedom and the second pentagonal mechanism offers three degrees of freedom of motion.

The first pentagonal mechanism defines a first axis through it's center, illustrated in FIG. 3 as the z axis. The first and the second pentagonal mechanisms are aligned along said first axis. (This is just to introduce axis z)

Attached to the first (4) and the second (6) pentagonal mechanism is an instrument driving means (8). The instrument driving means is adapted to hold a medical instrument and is adapted to permit the instrument to move along and rotate on its own axis; the instrument's axis is illustrated in FIG. 3 as the w axis.

The first pentagonal mechanism (4) consists of four bars assembled so as to permit movement of the pentagonal mechanism in two degrees of freedom.

It (4) is connected to the base (2) by two actuated joints (26 and 28). The first bar (10) is connected to the first actuated joint (26). The other end of the first bar (10) is connected to the second bar (12) by a passive revolute joint (34). The other end of the second bar is connected to the third bar (14) by a second passive revolute joint (36). The other end of the third bar (14) is connected to the fourth bar (16) by a third passive revolute joint (38). And finally the other end of the fourth bar is connected to the base by a second actuated joint (28).

The first (26) and the second (28) actuated joints can be driven by a first (54) and a second (56) driving means.

The second pentagonal mechanism (6) consists of four bars assembled so as to permit movement of the pentagonal mechanism in three degrees of freedom.

The second pentagonal mechanism (6) is connected to the base (2) by two actuated joints (30 and 32). The fifth bar (18) is connected to the third actuated joint (30). The other end of the fifth bar (18) is connected to the sixth bar (20) by a passive universal joint (42). The other end of the sixth bar (20) is connected to the seventh bar (22) by a passive revolute joint (40). The other end of the seventh bar (22) is connected to the eighth bar (24) by a second passive universal joint (44). And finally the other end of the eighth bar (24) is connected to the base (2) by a fourth actuated joint (32).

The third (30) and the fourth (32) actuated joints can be driven by a third (58) and a fourth (60) driving means.

The shape of the bars that constitute the first and second pentagonal mechanism can be adjusted so as to suite requirements of any particular application. They can be curved ("curved" is more suitable in geometrical sense) as illustrated in FIG. 3, but they could also be straight, or any other shape to suite the requirements.

The instrument driving means (8) comprises an instrument holding means. The instrument holding means is adapted to hold instruments such as needles, lasers and other suitable devices. The instrument illustrated in FIG. 3 is a brachytherapy needle (70).

It comprises a first connection means to connect it to the first pentagonal mechanism. In one embodiment of the invention two revolute joints are used (46 and 48). In another embodiment the first connection means could be designed as a suitably positioned universal joint.

It also comprises a second connection means to connect it to the second pentagonal mechanism so as to permit rotation in all directions. In one embodiment of the invention a spherical joint is used (50).

It also comprises an instrument moving means, which moves the instrument holding means along the instrument's axis, and an instrument rotating means, to permit the instrument to rotate on its axis (illustrated in FIG. 3 as w axis).

The instrument moving means (62) and the instrument rotating means (64) can be driven by a fifth (66) and a sixth driving means (68). The fifth driving means will cause the instrument to move along the w axis and the sixth driving means will cause the instrument to rotate on it.

The first (54) and the second (56) driving means permit movement of the first pentagonal mechanism so as to position the first connection means (46 and 48) as desired in a plane defined by a second axis and a third axis. Where the second axis is perpendicular to the first axis and the third axis is perpendicular to the first and the second axis; this plane is illustrated as the x-y plane in FIG. 3; the second axis is illustrated as the x and the third axis is illustrated as they axis.

The third (30) and the fourth (32) driving means permit movement of the second pentagonal mechanism (6) so as to position the second connection means (50) as desired in the x-y plane. And the universal joints (42 and 44) permit movement in a sagittal plane defined by the third and first axis; illustrated in FIG. 3 as the y-z plane.

As a result, when the instrument driving means (8) is assembled with the first and second pentagonal mechanism (4 and 6), it has four degrees of freedom of motion: its body can be moved up-down in the y-z plane, left-right in the x-y plane, rotated around the axis of the revolute joint (46), and rotated around the revolute joint (48).

The instrument driving means itself provides two degrees of freedom of motion to the instrument, relative to the instrument driving means' body. Thus, the instrument has a total of six degrees of freedom of motion in the x-y-z space, which is necessary and sufficient for achieving any desired position and orientation for it within the workspace of the apparatus.

The driving means can be connected to a computer (not illustrated) which would control their movement.

The invention claimed is:

1. An apparatus for the positioning and orientating of a medical instrument, comprising;
   a first mechanism having two degrees of freedom and consisting of first, second, third and fourth bars linked sequentially, the first mechanism rotationally connected at the first and fourth bars to a base by first and second actuated driven joints,
   a second mechanism having one degree of freedom more than the first mechanism and consisting of fifth, sixth, seventh and eighth bars linked sequentially, the second mechanism rotationally connected at the fifth and eighth bars to said base by third and fourth actuated driven joints,
   an instrument driving means,
   said instrument driving means being held by said first and second mechanisms, the instrument driving means adapted to hold a medical instrument and adapted to drive said instrument to move along its own axis and to rotate on its own axis where, the first bar is connected to the first actuated driven joint at one end, and by a first revolute joint to the second bar at the other end;

the second bar is connected to the first bar at one end, and by a second revolute joint to the third bar at the other end;

the third bar is connected to the second bar at one end, and by a third revolute joint to the fourth bar at the other end;

the fourth bar is connected to the third bar at one end, and to the second actuated driven joint at the other end;

the fifth bar is connected to the third actuated driven joint at one end, and by a first universal joint to the sixth bar at the other end;

the sixth bar is connected to the fifth bar at one end, and by a fourth revolute joint to the seventh bar at the other end;

the seventh bar is connected to the sixth bar at one end, and by a second universal joint to the fourth bar at the other end; and the eighth bar is connected to the seventh bar at one end, and to the fourth actuated driven joint at the other end.

2. The apparatus of claim 1 where;
the first, second, third and fourth actuated driven joints are revolute joints.

3. The apparatus of claim 2 where said instrument driving means is held by said first mechanism by a first connection means, and by said second mechanism by a second connection means.

4. The apparatus of claim 3 where the first connection means is two revolute joints.

5. The apparatus of claim 4 where the second connection means is a spherical joint.

6. The apparatus of claim 3 where the first connection means is a universal joint.

7. The apparatus of claim 3 where the first actuated driven joint is driven by a first driving means, the second actuated driven joint is driven by a second driving means, the first and the second driving means permit movement of the first mechanism so as to position the first connection means in a given position in a xy plane, the third actuated driven joint is driven by a third driving means and the fourth actuated driven joint is driven by a fourth driving means, the third and the fourth driving means permit movement of the second mechanism so as to position the second connection means in a given position in the xy plane.

8. The apparatus of claim 3 further comprising the medical instrument, wherein the first connection means attaches the medical instrument to one of the four bars of the first mechanism that is not connected to the base by respective actuated driven joints, and the second connection means attaches the medical instrument to one of the four bars of the second mechanism that is not connected to the base by respective actuated driven joints.

9. The apparatus of claim 3 further comprising the medical instrument, wherein the first connection means attaches the medical instrument to one of the four bars of the first mechanism other than the two bars that are respectively attached to the base by the first and second actuated driven joints and the second connection means attaches the medical instrument to one of the four bars of the second mechanism other than the two bars that are respectively attached to the base by the third and fourth actuated driven joints.

10. The apparatus of claim 1, 2, 3, 4, 6, 5, or 7 where the instrument driving means comprises;
a holding means,
a fifth driving means to move said holding means in the direction of the axis of said instrument,
a sixth driving means to rotate said instrument about said instrument's axis.

11. The apparatus of claim 10 where said instrument is a laser beam delivering device.

12. The apparatus of claim 10 where said instrument is a needle.

13. The apparatus of claim 1 wherein one or more of: the instrument driving means, and the actuated driven joints rotationally connecting the first and second mechanisms to the base, are computer controlled; or the instrument driving means, and the actuated driven joints rotationally connecting the first and second mechanisms to the base, are jointly computer controlled.

14. The apparatus of claim 1 wherein the size of the four sequentially linked bars of the first and second mechanisms are selected to control a workspace.

15. The apparatus of claim 1 further comprising the medical instrument.

* * * * *